United States Patent [19]

Kametani et al.

[11] 4,281,175

[45] Jul. 28, 1981

[54] PROCESS FOR PRODUCING DIMETHYLAMINOETHYL METHACRYLATE

[75] Inventors: Yoshiya Kametani; Yasuo Iino, both of Yokohama, Japan

[73] Assignee: Nitto Chemical Industry Co., Ltd., Tokyo, Japan

[21] Appl. No.: 160,367

[22] Filed: Jun. 17, 1980

Related U.S. Application Data

[63] Continuation of Ser. No. 802,901, Jun. 2, 1977, abandoned.

[30] Foreign Application Priority Data

Jun. 18, 1976 [JP] Japan .................................. 51-71009

[51] Int. Cl.$^3$ ............................................. C07C 67/02
[52] U.S. Cl. .................................................. 560/217
[58] Field of Search ................... 560/217, 222, 99, 234

[56] References Cited

U.S. PATENT DOCUMENTS

| | | | |
|---|---|---|---|
| 2,720,507 | 10/1955 | Caldwell | 260/429.7 |
| 3,341,570 | 9/1967 | Barie, Jr. | 560/99 |
| 3,642,877 | 2/1972 | Jayawant | 560/217 |
| 3,714,434 | 1/1973 | White | 560/217 |

FOREIGN PATENT DOCUMENTS

577788  6/1959  Canada .

OTHER PUBLICATIONS

Decision of Board of Appeals, dtd. Apr. 21, 1980.

*Primary Examiner*—Joseph E. Evans
*Assistant Examiner*—L. Hendriksen
*Attorney, Agent, or Firm*—Cushman, Darby & Cushman

[57] ABSTRACT

Methyl methacrylate is transesterified with dimethylaminoethanol using alkyltin compounds as catalysts. Typical alkyltin compounds used are tetrabutyltin, trioctyltin ethoxide, dibutyltin dimethoxide, dibutyltin dihydride, dibutyltin dilaurate, dibutyltin maleate, bis(tributyltin) oxide and bis(dibutylmethoxytin) oxide.

9 Claims, No Drawings

PROCESS FOR PRODUCING DIMETHYLAMINOETHYL METHACRYLATE

This is a continuation of application Ser. No. 802,901 filed June 2, 1977, now abandoned.

The present invention relates to a process for producing dimethylaminoethyl methacrylate which comprises subjecting methyl methacrylate and dimethylaminoethanol to transesterification.

The process for producing dimethylaminoethyl methacrylate which comprises subjecting methyl methacrylate and dimethylaminoethanol to transesterification is known and proceeds as represented by the following reaction formula,

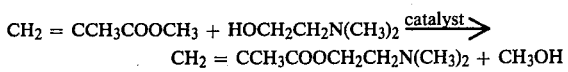

$$CH_2 = CCH_3COOCH_3 + HOCH_2CH_2N(CH_3)_2 \xrightarrow{catalyst}$$
$$CH_2 = CCH_3COOCH_2CH_2N(CH_3)_2 + CH_3OH$$

It is generally known to use in the transesterification reaction an alkali metal alkoxide such as sodium methoxide ($NaOCH_3$) as a catalyst.

If the said transesterification reaction is performed in the presence of an alkali metal alkoxide as a catalyst, however, the activity of the catalyst is reduced during the reaction and thereby the catalyst must be replenished many times during the reaction. It is very troublesome.

Also, these catalysts have defects in that they cause during the reaction a side reaction of adding dimethylaminoethanol as a starting material or methanol formed as a by-product to the double bond in methyl methacrylate as a starting material and that they cause also, when the reaction mixture is distilled after the reaction to recover the desired product, a side reaction of adding the unreacted alcohol or the alcohol formed as a by-product to the double bond in the dimethylaminoethyl methacrylate as a desired product.

Alternatively, the use of a titanium alkoxide is a catalyst is proposed. This catalyst is expensive and its activity is lost by the presence of a very small amount of moisture in the reaction system. Therefore, the moisture in the reaction system must be previously removed completely when these catalysts are used.

Further, the use of di-n-butyltin oxide as a catalyst is proposed in U.S. Pat. No. 3,642,877. The activity of the catalyst is also lost by the presence of a small amount of moisture in the reaction system. Also, the reaction velocity can not be increased since the catalyst is slow in development of its activity.

An object of the present invention is to produce dimethylaminoethyl methacrylate more advantageously than by prior art processes by transesterification between methyl methacrylate and dimethylaminoethanol by the use of a catalyst which has not the above-mentioned defects of the prior art catalysts. The process of the present invention is characterized by using as a catalyst in the said transesterification reaction at least one member selected from the group consisting of (I) compounds represented by the formula

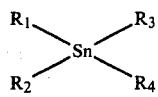

wherein $R_1$, $R_2$, $R_3$ and $R_4$ each are an alkyl group having 1 to 12 carbon atoms or phenyl group, (II) compounds represented by the formula

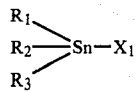

wherein $R_1$, $R_2$ and $R_3$ are as defined above and $X_1$ is —H, —$OR_1$, —$SR_1$, —$S(CH_2)_nCOOR_1$ (n is 1 or 2), —$OCOR_1$ or —OCOCH=CHCOOR_1$, (III) compounds represented by the formula

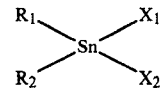

wherein $R_1$, $R_2$ and $X_1$ are as defined above and $X_2$ has the same definition as that of $X_1$, (IV) compounds represented by the formulae

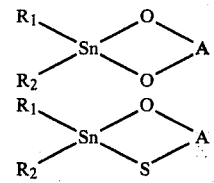

wherein $R_1$ and $R_2$ are as defined above and A is —COCH=CHOC—, —$CH_2OC$— or —$CH_2CH_2$—, and (V) compounds represented by the formula

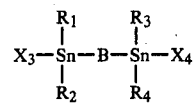

wherein $R_1$, $R_2$, $R_3$ and $R_4$ are as defined above, $X_3$ and $X_4$ each are —H, —$R_1$, —$OR_1$, —$SR_1$, —$S(CH_2)_n$—$COOR_1$ (n is 1 or 2), —$OCOR_1$ or —OCOCH=CHCOOR_1$, and B is —OCOCH=CHCOO—, —$OCH_2CH_2)_nO$—, —$SCH_2CO$—$OCH_2CH_2)_nOCOCH_2S$— (n is 1 or 2) or —O—.

According to the present invention, such a side reaction as the addition of dimethylaminoethanol or methanol to the double bond in methyl methacrylate or the desired product does not substantially occur during the entire process. Thereby, it is possible to obtain the desired product in a high yield.

Also, the catalysts used in the present invention do not loss their activity during the reaction. Therefore, the catalysts may be added to the reaction system at once when the reaction is started. Thus, the operation is simple.

Further, the catalysts used in the present invention are less affected by the presence of a very small amount of moisture in the reaction system than prior art catalysts. Therefore, it is unnecessary to remove the moisture in the reaction system completely prior to the reaction.

Also, many of the catalysts used in the present invention are used as a stabilizer for polyvinyl chloride resin or a pesticide or a raw material for the production thereof. Therefore, they are usually commercially available.

As the compounds represented by the formula

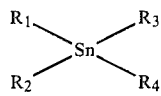

wherein $R_1$, $R_2$, $R_3$ and $R_4$ each are an alkyl group having 1 to 12 carbon atoms or phenyl group, used as a catalyst in the present invention, there are many examples but tetramethyl tin, tetraethyl tin, tetrabutyl tin, tetraoctyl tin and tetraphenyl tin are preferable.

Examples of the compounds represented by the formula

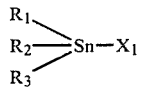

wherein $R_1$, $R_2$ and $R_3$ each are an alkyl group having 1 to 12 carbon atoms or phenyl group, and $X_1$ is —H, —$OR_1$, —$SR_1$, —$S(CH_2)_nCOOR_1$ (n is 1 or 2), —O-$COR_1$ or —OCOCH=CHCOOR$_1$, include triphenyltin methoxide, triphenyltin ethoxide, triphenyltin butoxide, triphenyltin acetate, triphenyltin hydride, tributyltin methoxide, tributyltin ethoxide, tributyltin butoxide, tributyltin hydride, tributyltin acetate, trioctyltin hydride, trioctyltin methoxide, trioctyltin ethoxide, trioctyltin butoxide, and trioctyltin acetate.

Examples of the compounds represented by the formula

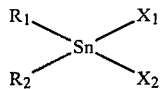

wherein $R_1$ and $R_2$ each are an alkyl group having 1 to 12 carbon atoms or phenyl group, and $X_1$ and $X_2$ each are —H, —$OR_1$, —$SR_1$, —$S(CH_2)_nCOOR_1$ (n is 1 or 2), —$OCOR_1$ or —OCOCH=CHCOOR$_1$, include dibutyltin dimethoxide, dibutyltin diethoxide, dibutyltin dibutoxide, dibutyltin dihydride, dibutyltin diacetate, dibutyltin dilaurate, dioctyltin dimethoxide, dioctyltin diethoxide, dioctyltin dibutoxide, dioctyltin dihydride, dioctyltin diacetate, and dioctyltin dilaurate.

Examples of the compounds represented by the formula,

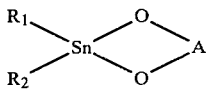

wherein $R_1$ and $R_2$ each are an alkyl group having 1 to 12 carbon atoms or phenyl group, and A is —COCH=CHOC—, —CH$_2$OC— or —CH$_2$CH$_2$—, include dibutyltin maleate, dioctyltin maleate, dibutyltin ethylenealkoxide, and dioctyltin ethylenealkoxide.

Examples of the compounds represented by the formula,

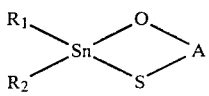

wherein $R_1$ and $R_2$ each an alkyl group having 1 to 12 carbon atoms or phenyl group, and A is —COCH=CHOC—, —CH$_2$OC— or —CH$_2$CH$_2$—, include dibutyltin thioglycolate, dibutyltin thiopropionate, dioctyltin thioglycolate, and dioctyltin thiopropionate.

Examples of the compounds represented by the formula

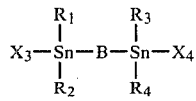

wherein $R_1$, $R_2$, $R_3$ and $R_4$ each are an alkyl group having 1 to 12 carbon atoms or phenyl group, $X_3$ and $X_4$ each are —H, —$R_1$, —$OR_1$, —$SR_1$, —$S(CH_2)_nCOOR_1$ (n is 1 or 2), —$OCOR_1$ or —OCOCH=CH-COOR$_1$, and B is —OCOCH=CHCOO—, —OCH$_2$CH$_2)_nO—, —SCH$_2$CO—OCH$_2$CH$_2)_nOCOCH_2S$— (n is 1 or 2) or —O—, include bis(tributyltin) maleate, bis(tributyltin) oxide, bis(tributyltin) ethylenealkoxide, bis(tributyltin) ethyleneglycol dithioglycolate, bis(dibutylmethoxytin) maleate, bis(dibutylmethoxytin) oxide, bis(dibutylmethoxytin) ethylenealkoxide, bis(dibutylmethoxytin) ethyleneglycoldithioglycolate, bis(dibutylethoxytin) maleate, bis(dibutylethoxytin) oxide, bis(dibutylethoxytin) ethylenealkoxide, bis(dibutylethoxytin) ethyleneglycoldithioglycolate, bis(dibutylbutoxytin) maleate, bis(dibutyllauroxytin) maleate, bis(dibutoxytin) oxide, bis(dibutylbutoxytin) ethylenealkoxide, bis(dibutylbutoxytin) ethyleneglycoldithioglycolate, bis(trioctyltin) maleate, bis(trioctyltin) oxide, bis(trioctyltin) ethylenealkoxide, bis(trioctyltin) ethyleneglycoldithioglycolate, bis(dioctylmethoxytin) maleate, bis(dioctylmethoxytin) oxide, bis(dioctylmethoxytin) ethylenealkoxide, bis(dioctylmethoxytin) ethyleneglycoldithioglycolate, and bis(dioctyllauroxytin) maleate.

The amount of the above-mentioned catalysts used in the practice of the present invention is usually 0.1 to 5% by mole, and preferably 0.25 to 2.5% by mole, based on the amount of dimethylaminoethanol as a starting material. The catalysts used in the present invention are generally soluble in the reactants. Thereby, the development of their catalytic activity is rapid and the reaction velocity of the reaction between methyl methacrylate and dimethylaminoethanol can be increased.

The amount of methyl methacrylate used is usually 1.2 to 3.5 moles per mole of dimethylaminoethanol.

In the reaction, a polymerization inhibitor is added to prevent the polymerization of methyl methacrylate as a starting material and dimethylaminoethyl methacrylate as a desired product. The polymerization inhibitors generally used include phenothiazine and hydroquinone monomethyl ether.

The reaction temperature is usually 80° to 130° C. At temperatures of less than 80° C., the activity of the catalysts is low. Also, the reaction temperature of more than 130° C. is not preferable in that side reactions such as polymerization, etc. are apt to occur at such a temperature.

Although the reaction may be conducted under atmospheric pressure, it is preferable to carry out the reaction under a slightly reduced pressure since the methanol formed as a by-product can be rapidly distilled off from the reaction system.

In the practice of the reaction, it is unnecessary to supply the catalysts in portions but a required amount of the catalysts may be added at a stretch on the start of the reaction.

The reaction solvent is generally not required, but may be used. Examples of the solvents used include benzene, toluene and hexane.

The methanol as formed as a by-product in the reaction shows azeotropy with the unreacted methyl methacrylate. During the reaction, therefore, the azeotropic mixture is led to a distilling column where part of the mixture is withdrawn from the reaction system while the mixture is refluxed into the reaction system at a suitable reflux ratio. The reflux ratio is usually decided to be 1:1 to 10:1.

General embodiment of the present invention will be explained. First of all, appointed amounts of starting materials, a catalyst, a polymerization inhibitor, and optionally a solvent are charged into and heated in a reactor equipped with a thermometer and a distilling column. The mixture is reacted for some time under complete reflux (the temperature of the liquid about 100° C.). At the point where reflux became violent, part of the azeotric mixture of methanol and methyl methacrylate is withdrawn from the system at a reflux ratio of about 5:1. During the reaction, the temperature at the top of the distilling column is kept at about 55° to 70° C.

With the progress of the reaction, the temperature at the top of the distilling column and the temperature of the reaction mixture increase. In order to prevent side reactions and the formation of polymers, it is desirable to keep the temperature of the reaction mixture at 130° C. or less.

The reaction time varies according to a molar ratio of the starting materials, the reaction temperature, a reflux ratio, etc., but is usually within 6 hours. When the reaction approaches the end, the temperature at the top of the distilling column increases suddenly.

The state of the reaction may be checked by measuring the conversion of dimethylaminoethanol as a starting material in the reaction liquid by gas chromatography.

After the reaction, the reaction mixture is distilled under reduced pressure according to a usual method. The unreacted methyl methacrylate is first distilled off and the desired product, dimethylaminoethyl methacrylate, is then distilled off.

Dimethylaminoethyl methacrylate produced according to the present invention are a compound useful as a raw material for the production of cationic polymers which may be used as an antistatic agent, a soil improving agent, an electroconductive processing agent, a paper treating agent, a flocculant, etc.

The following examples illustrate the present invention.

EXAMPLE 1

Into a flask equipped with a stirrer, a thermometer and a packed column are charged 187 g of methyl methacrylate, 66.8 g of dimethylaminoethanol, 1.5 g of phenothiazine as a polymerization inhibitor, and 3.5 g of dibutyltin diethoxide as a catalyst. The mixture is heated to boiling while the pressure of the reaction system is kept constant at 560 mmHg.

The azeotropic mixture of the methanol formed and methyl methacrylate is subjected to complete reflux for about 5 minutes. Then, the reaction mixture is reacted while part of the azeotropic mixture is removed from the system at a reflux ratio of 5:1. During the reaction, the temperature at the top of the distilling column is kept at 56° to 60° C. The transesterification reaction is completed in 3 hours.

After the reaction, the reaction mixture is distilled under reduced pressure to obtain 114.1 g of a fraction at 72° C. at 18 mmHg to 63.3° C. at 5 mmHg.

As a result of the analysis of this fraction by gas chromatography, infrared spectroscopic analysis, and nuclear magnetic resonance, it is confirmed that the fraction is dimethylaminoethyl methacrylate. The yield of dimethylaminoethyl methacrylate is 96.8% based on the starting dimethylaminoethanol.

EXAMPLE 2

Into a reactor equipped with a stirrer, a thermometer and a distilling column are charged 760 g of methyl methacrylate, 268 g of dimethylaminoethanol, 6.2 g of phenothiazine as a polymerization inhibitor and 20.8 g of dibutyltin maleate as a catalyst. The mixture is heated to boiling with stirring.

The azeotropic mixture of the methanol formed and methyl methacrylate is subjected to complete reflux for about 5 minutes. The reaction mixture is then reacted while part of the azeotropic mixture is removed from the system at a reflux ratio of 5:1. During the reaction, the temperature at the top of the distilling column is kept at 65° to 70° C.

After the reaction, the reaction mixture is distilled under reduced pressure in the same manner as in Example 1 to obtain 438 g of dimethylaminoethyl methacrylate. The yield of dimethylaminoethyl methacrylate is 92.6% based on dimethylaminoethanol.

EXAMPLES 3-9

Dimethylaminoethyl methacrylate is prepared in the same manner as in Example 1 except that tetrabutyltin, triphenyltin ethoxide, dibutyltin dihydride, dibutyltin dilaurate, dibutyltin dithioglycolate, bis(dibutyllauroxytin) maleate or bis(tributyltin) oxide alone is respectively used as a catalyst.

The results obtained are shown in Table 1. In Table 1, "Yield of desired product" is the yield of dimethylaminoethyl methacrylate obtained in each example based on the starting dimethylaminoethanol.

TABLE 1

| Example | Catalyst used Name | Amount (g) | Reaction time (hours) | Yield of desired product (%) |
|---|---|---|---|---|
| 3 | Tetrabutyltin | 5 | 5 | 95.0 |
| 4 | Triphenyltin ethoxide | 5 | 6 | 88.8 |
| 5 | Dibutyltin dihydride | 5 | 4 | 96.3 |
| 6 | Dibutyltin dilaurate | 6 | 5.5 | 89.9 |
| 7 | Dibutyltin dithioglycolate | 6 | 5 | 69.3 |
| 8 | Bis(dibutyllauroxytin) maleate | 6 | 6 | 87.6 |
| 9 | Bis(tributyltin) oxide | 5 | 5 | 90.2 |

Among the catalysts used in the respective examples, the catalysts used in Examples 3, 4, 5, 8 and 9 were synthesized according to known processes. The other catalysts used were commercially available.

COMPARATIVE EXAMPLE

Dimethylaminoethyl methacrylate is prepared in the same manner as in Example 1 except that 0.8 g of sodium methoxide is used as a catalyst. The reaction time is 1.5 hours.

After the reaction, the reaction mixture is distilled under reduced pressure. The analysis of the reaction product shows that the conversion of the starting dimethylaminoethanol was 92.4% but the yield of dimethylaminoethyl methacrylate was only 58.7% based on the starting dimethylaminoethanol. Further, a considerable amount of by-products such as methoxy-iso-butyric acid methyl ester, methoxy-iso-butyric acid dimethylaminoethyl ester, dimethylaminoethoxy-iso-butyric acid dimethylaminoethyl ester and sodium methacrylate, etc. is observed.

What is claimed is:

1. A process for producing dimethylaminoethyl methacrylate which comprises transesterifying methyl methacrylate with dimethylaminoethanol with a catalyst selected from the group consisting of tetrabutyltin, trioctyltin ethoxide, dibutyltin dimethoxide, dibutyltin diethoxide, dibutyltin dihydride, dibutyltin dilaurate, dioctyltin dilaurate, dibutyltin maleate, dioctyltin maleate bis(tributyltin) oxide, bis (dibutylmethoxytin) oxide and bis (dioctylmethoxytin) oxide.

2. A process according to claim 1 wherein the catalyst is tetrabutyltin.

3. A process according to claim 1 wherein the catalyst is dibutyltin dimethoxide.

4. A process according to claim 1 wherein the catalyst is dibutyltin dimethoxide, dibutyltin diethoxide, dibutyltin dihydride, dibutyltin dilaurate, or dioctyltin dilaurate.

5. A process according to claim 4 wherein the catalyst is dibutyltin dimethoxide.

6. A process according to claim 4 wherein the catalyst is dibutyltin diethoxide.

7. A process according to claim 4 wherein the catalyst is dibutyltin dihydride.

8. A process according to claim 1 wherein the catalyst is bis(tributyltin) oxide, bis (dibutylmethoxytin) oxide, or bis(dioctylmethoxytin) oxide.

9. A process according to claim 1 wherein the catalyst is dibutyltin maleate or dioctyltin maleate.

* * * * *